(12) United States Patent
Draper et al.

(10) Patent No.: US 9,436,298 B2
(45) Date of Patent: Sep. 6, 2016

(54) EXTENDABLE MOUTH STYLUS

(71) Applicant: United States Government as Represented by The Department of Veterans Affairs, Washington, DC (US)

(72) Inventors: Ursula Draper, Tampa, FL (US); Michael Kerrigan, Tampa, FL (US); Jeffrey Craighead, Land-O-Lakes, FL (US); Jan Jasiewicz, Tampa, FL (US); Telina Caudill, Tampa, FL (US)

(73) Assignee: The United States of America as Represented by The Department of Veterans Affairs, Washington, DC (US)

( * ) Notice: Subject to any disclaimer, the term of this patent is extended or adjusted under 35 U.S.C. 154(b) by 154 days.

(21) Appl. No.: 14/180,988

(22) Filed: Feb. 14, 2014

(65) Prior Publication Data

US 2014/0232701 A1     Aug. 21, 2014

Related U.S. Application Data

(60) Provisional application No. 61/765,532, filed on Feb. 15, 2013.

(51) Int. Cl.
| | | |
|---|---|---|
| *G06F 3/0354* | (2013.01) | |
| *A61F 4/00* | (2006.01) | |
| *G06F 3/039* | (2013.01) | |

(52) U.S. Cl.
CPC ............. *G06F 3/03545* (2013.01); *A61F 4/00* (2013.01); *G06F 3/039* (2013.01)

(58) Field of Classification Search
CPC .................................................. G06F 3/03545
See application file for complete search history.

(56) References Cited

U.S. PATENT DOCUMENTS

| | | | | | |
|---|---|---|---|---|---|
| 3,653,775 A | * | 4/1972 | Ross | .......................... | A61F 4/00 131/186 |
| 3,795,281 A | * | 3/1974 | Cloran | ...................... | A61F 4/00 173/30 |
| 4,496,126 A | * | 1/1985 | Melton | .................. | A47B 23/06 248/445 |
| 4,828,418 A | * | 5/1989 | Sauer | ........................ | A61F 4/00 173/30 |
| 5,422,640 A | * | 6/1995 | Haley | ...................... | B41J 7/005 340/4.11 |
| 5,485,357 A | * | 1/1996 | Zolninger | .................. | A61F 4/00 362/103 |
| 5,689,246 A | * | 11/1997 | Dordick | ................... | H01H 3/14 340/4.11 |
| 5,860,754 A | * | 1/1999 | Garland | ............... | B43K 23/004 401/6 |

(Continued)

*Primary Examiner* — Claire X Pappas
*Assistant Examiner* — Robert Stone
(74) *Attorney, Agent, or Firm* — Procopio, Cory, Hargreaves & Savitch LLP; Pattric J. Rawlins

(57) ABSTRACT

An extendable stylus operated with a mouth, the stylus having an extending portion configured to have an adjustable length, a conductive tip that can interface with a touch screen device, the conductive tip located at a first end of the extending portion, a mouthpiece that engages the mouth of a user, wherein the mouthpiece is located at a second end of the extending portion opposite the first end and a control mechanism disposed at or near the second end of the extending portion, wherein the control mechanism is configured to control the length of the extending portion based on an operation by the mouth of the user.

19 Claims, 11 Drawing Sheets

(56) References Cited

U.S. PATENT DOCUMENTS

| | | | | |
|---|---|---|---|---|
| 6,220,559 B1* | 4/2001 | Chow | | A47B 23/007 248/445 |
| 6,222,524 B1* | 4/2001 | Salem | | A61F 4/00 340/4.11 |
| 6,801,231 B1* | 10/2004 | Beltz | | G06F 3/011 340/4.11 |
| 7,768,499 B2* | 8/2010 | Sturtz | | G06F 3/011 341/20 |
| D662,098 S * | 6/2012 | Leto | | D14/411 |
| 2007/0085827 A1* | 4/2007 | Sturtz | | G06F 3/011 345/157 |
| 2009/0309747 A1* | 12/2009 | Ghovanloo | | A61F 4/00 340/686.1 |
| 2009/0315348 A1* | 12/2009 | Diebold | | A61F 4/00 294/219 |
| 2011/0162894 A1* | 7/2011 | Weber | | G06F 3/044 178/19.03 |

\* cited by examiner

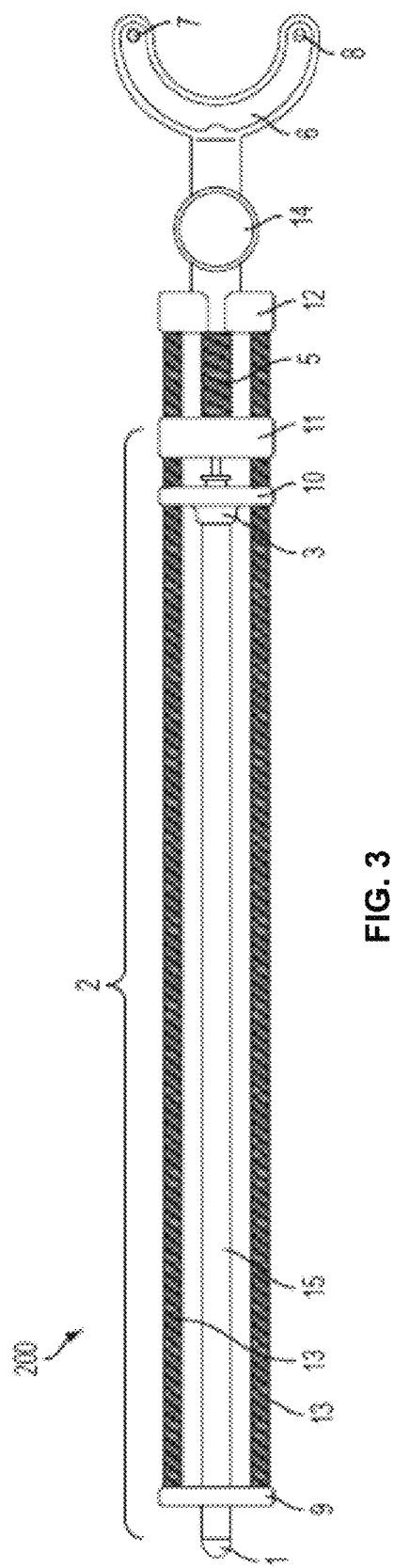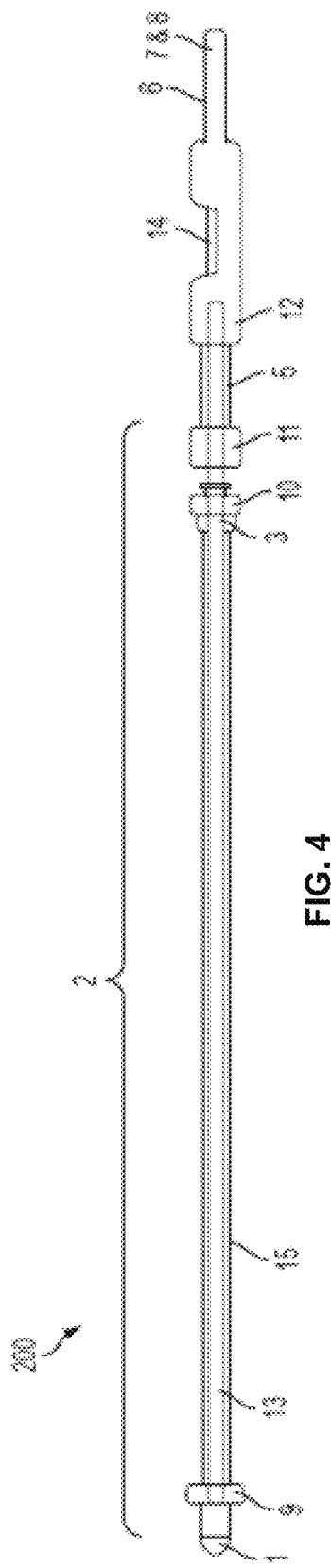
FIG. 3
FIG. 4

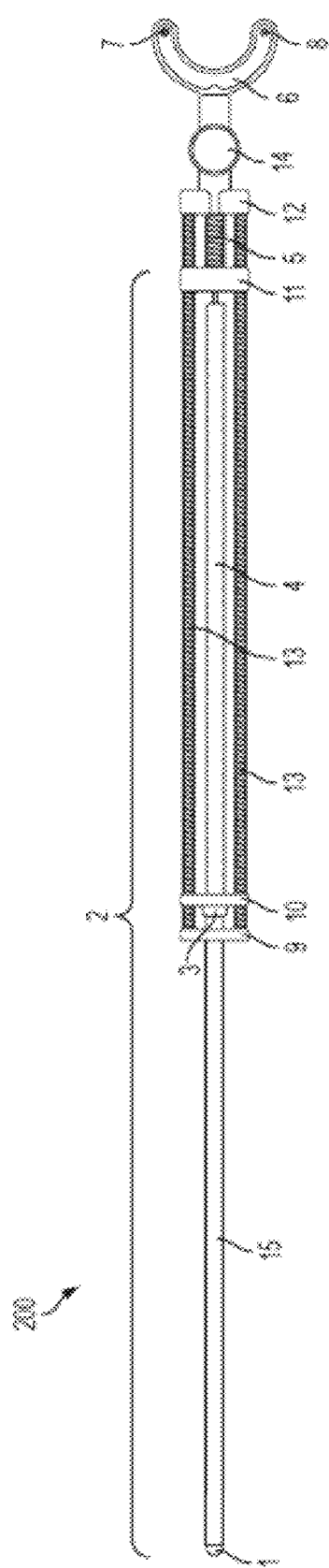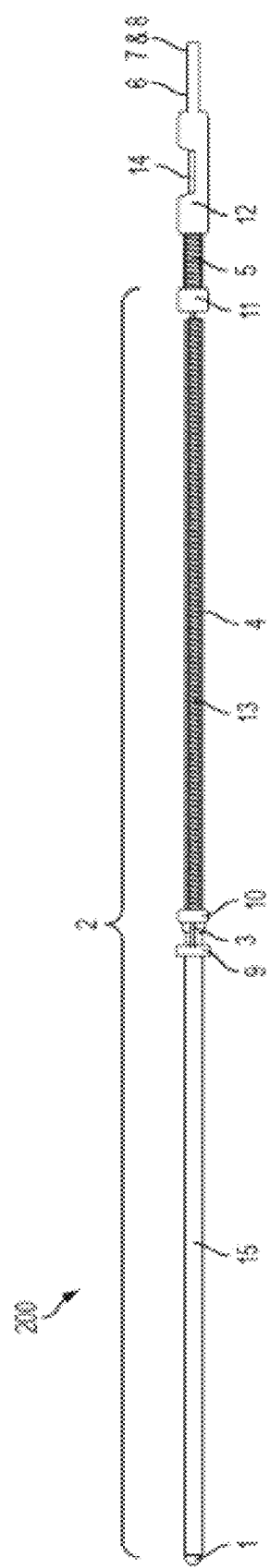
FIG. 6
FIG. 7

EXTENDABLE MOUTH STYLUS

CROSS-REFERENCE TO RELATED APPLICATIONS

This application claims benefit of priority from Provisional U.S. Patent application Ser. No. 61/765,532, filed Feb. 15, 2013, the contents of which are incorporated by reference.

BACKGROUND

1. Field of the Invention

The present invention is generally related to mouth styli and more particularly related to an electronically or mechanically extendable mouth stylus.

2. Related Art

Mouth Styli designed to allow quadriplegic and tetraplegic patients to interact with touch screen devices are commercially available. To use a mouth stylus, the stylus is placed in an individual's mouth and is used to point and interact with the touch sensitive device by pressing on the icon controls.

However, commercially available mouth styli are of fixed length as shown in FIG. 1. The fixed length of existing mouth styli can create problems for paralyzed individuals who must move their head to compensate for changes in length between the head/mouth and the touch sensitive device.

Therefore, there is a need for a mouth stylus that may overcome this problem found in the conventional systems described above. Thus, to address this problem, a mouth stylus may need to change length to help quadriplegic and tetraplegic patients interact with the touch screen device.

SUMMARY

A general purpose of a mouth stylus device is to allow someone who is unable to use his or her limbs to operate a touch sensitive device. Various embodiments of a mouth stylus having an extendable portion are described herein. Some embodiments are purely mechanical allowing a user to actuate a spring or lever with at least one of their mouth, teeth, or tongue to extend and retract the stylus. Though mechanical embodiments can be operated successfully, some also may cause potential discomfort for individuals. Thus, some embodiments use a motor controlled by a user to vary the length of the stylus through the application of force to the mouthpiece or articulation of a lever integrated into the mouth piece with the tongue, teeth or jaw.

A solution described herein may also include a mechanically actuated mouth stylus designed to be used with both capacitive and resistive touch screens by users who are unable to control their limbs. In some embodiments, the mechanically actuated mouth stylus includes a movable portion linearly coupled to a stationary portion by a spring loaded locking mechanism. In some embodiments, the locking mechanism is mechanically coupled to a spring loaded mouthpiece assembly such that applying bite pressure to the mouthpiece assembly causes the locking mechanism to release allowing the moveable portion to move relative to the stationary portion by application of either gravity or blowing pressure.

A solution described herein may also include an electromechanically actuated mouth stylus, designed to enable the use of both capacitive and resistive touch screens by users who are unable to control their limbs. In some embodiments, an electromechanically actuated mouth stylus uses a small direct current (DC) motor coupled to a linear actuator. In some embodiments, an electromechanically actuated mouth stylus uses a DC motor coupled to a spool of string to compress or release a linear spring and retract or extend a plurality of telescoping pieces. In some embodiments, applying pressure to either the left or right side of the mouthpiece using the jaw controls the shaft extension and retraction. For instance, lengthening is achieved by applying higher pressure to the right side of the mouthpiece while shortening is achieved by applying higher pressure to the left side of the mouthpiece. In some embodiments, the tip of the device is covered in a conductive plastic or rubber to enable use on capacitive touch screens. An electromechanically actuated device may provide greater controllability and pressure when touching the screen compared to a purely mechanical device that could be actuated using the tongue or pneumatic pressure from the lungs. However, an electromechanically actuated embodiment need not provide greater control or pressure application compared to a purely mechanical embodiment.

Other features and advantages of the present invention will become more readily apparent to those of ordinary skill in the art after reviewing the following detailed description and accompanying drawings.

BRIEF DESCRIPTION OF THE DRAWINGS

The structure and operation of the present invention will be understood from a review of the following detailed description and the accompanying drawings in which like reference numerals refer to like parts and in which:

FIG. 3 is a top view diagram according to a second example embodiment of an extendable mouth stylus in a non-extended state;

FIG. 4 is a side view diagram according to the second example embodiment of the extendable mouth stylus in the non-extended state;

FIG. 6 is a top view diagram according to the second example embodiment of the extendable mouth stylus in an extended state;

FIG. 7 is a side view diagram according to the second example embodiment of the extendable mouth stylus in the extended state;

DETAILED DESCRIPTION

Certain embodiments disclosed herein provide for an extendable mouth stylus that allows use of both capacitive and resistive touch screens by users having limited or no control of their limbs. For example, one apparatus disclosed herein provides an electromechanically extendable mouth stylus that allows a user to extend and retract a conductive tip by applying pressure to different portions of a mouthpiece. After reading this description it will become apparent to one skilled in the art how to implement the invention in various alternative embodiments and alternative applications. However, although various embodiments of the present invention will be described herein, it is understood that these embodiments are presented by way of example only, and not limitation. As such, this detailed description of various alternative embodiments should not be construed to limit the scope or breadth of the present invention as set forth in the appended claims.

Electromechanically Extendable Mouth Stylus

Figure 1:
FIG. 1 is illustrates a prior art mouth stylus.
Figure 2:
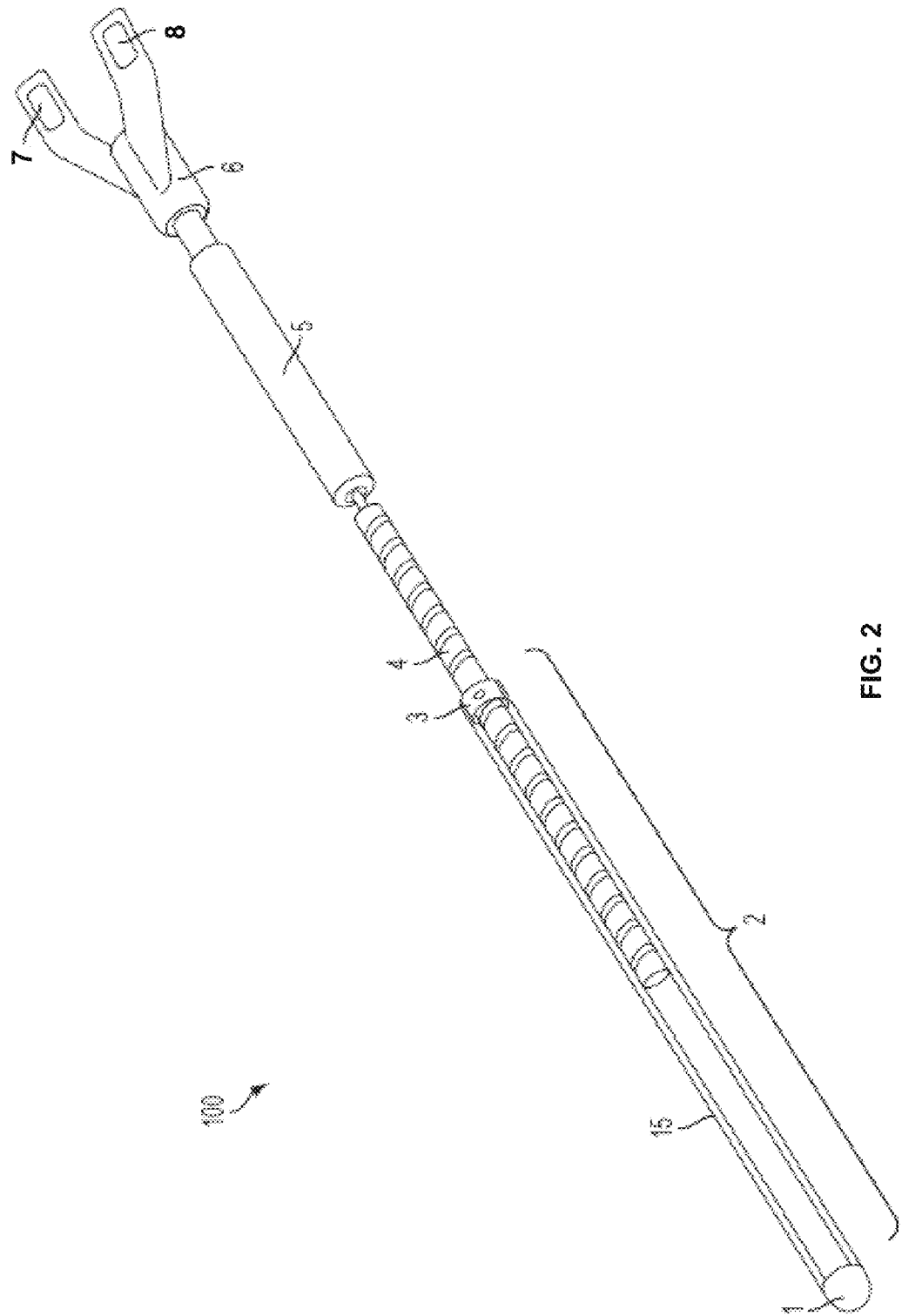
FIG. 2 is a plan view diagram illustrating a first example extendable mouth stylus according to an embodiment of the invention.

FIG. 2 illustrates a plain view diagram illustrating a first example embodiment of an extendable mouth stylus 100. The extendable mouth stylus includes a flexible, conductive tip 1, an extending portion 2, a mouthpiece 6, and one or more control mechanism 7 and 8 integrated into the mouthpiece 6. In this embodiment, the extending portion 2 includes a linear member 15, a nut 3 attached to the linear member 15, a power screw 4 rotatable relative to the nut 3 and the linear member 15, and a motor 5 disposed between the power screw 4 and the mouthpiece 6.

The conductive tip 1 may be formed from a material capable of conducting capacitance from a human user to a touch screen device in order to simulate the dielectric difference typically offered by a human appendage. In other words, the stylus may be capable of conducting capacitance along its entire length between the user and the touch screen device so that the dielectric difference necessary to operate the capacitive screens can be maintained. Examples of potential materials for the conductive tip 1 include, but are not limited to natural or synthetic rubbers, plastic polymers (such as polypropylene), and metallic materials (such as aluminum). However, embodiments of the present application need not be required to conduct capacitance along their entire length and embodiments may include the conductive tip 1 being electrically isolated from the mouthpiece 6.

The conductive tip 1 may be formed to have a hemispherical or dome shape, but is not particularly limited to this shape. Alternatively, the tip may be formed to have a cylindrical shape, a conical shape, or any other shape apparent to a person of ordinary skill in the art. In some embodiments, the conductive tip 1 may be formed to have a diameter equal to or greater than one-quarter (0.25) inch. However, the tip is not specifically limited to this size and could have any size selected by a person of ordinary skill in the art.

As discussed above, in this embodiment, the extending portion 2 may include a linear member 15, a nut 3 attached to the linear member 15, a power screw 4 rotatable relative to the nut 3 and the linear member 15, and a motor 5 disposed between the power screw 4 and the mouthpiece 6. The linear member 15 may be formed as a generally cylindrical shaft, with conductive tip 2 attached at one end. However, the linear member is not limited to a generally cylindrical shape, and may have any shape as would be apparent to a person of ordinary skill in the art. The conductive tip 2 may be attached by various methods including, but not limited to adhesive attachment, a threaded screw, welding, press fitting or any other attachment method apparent to a person of ordinary skill in the art. The nut 3 may be attached to the linear member 15 at an opposite end from the conductive tip 2. The nut 3 may be attached to the linear member 15 by various methods including adhesive, threaded screw, welding, press fitting, or any other attachment method apparent to a person of ordinary skill in the art.

In some embodiments, the linear member 15 may have an at least partially hollow interior configured to receive at least a portion of the power screw 4 therein. However, the linear member 15 is not required to be hollow, nor is it required to receive any portion of the power screw 4. The linear member 15 may be formed from any material capable of conducting capacitance from a human user to a touch screen device in order to simulate the dielectric difference typically offered by a human appendage. Examples of potential materials for the linear member 15 include, but are not limited to natural or synthetic rubbers, plastic polymers (such as polypropylene), and metallic materials (such as aluminum). However, embodiments of the present application need not be required to conduct capacitance along their entire length and embodiments may include the conductive tip 1 being electrically isolated from the mouthpiece 6. Alternatively, the linear member 15 may be formed of any material, including the lightest materials available and/or non-conductive materials. In an embodiment of the mouth stylus having the linear member 15 formed from non-conductive materials, a conductor, such as a metallic wire may be provided to maintain the dielectric difference across the length of the stylus.

The shape of the nut 3 is not particularly limited, and may include hexagonal, octagonal, cylindrical, or any other shape apparent to a person of ordinary skill in the art. Additionally, the nut 3 may have a threaded interior in some embodiments. The nut 3 may be formed from any material capable of conducting capacitance from a human user to a touch screen device in order to simulate the dielectric difference typically offered by a human appendage. Examples of potential materials for the nut 3 include, but are not limited to natural or synthetic rubbers, plastic polymers (such as polypropylene), and metallic materials (such as aluminum). However, embodiments of the present application need not be required to conduct capacitance along their entire length and embodiments may include the conductive tip 1 being electrically isolated from the mouthpiece 6. Alternatively, the nut 3 may be formed of any material, including the lightest materials available and/or non-conductive materials. In an embodiment of the mouth stylus having the linear nut 3 formed from non-conductive materials, a conductor, such as a metallic wire may be provided to maintain the dielectric difference across the length of the stylus.

The power screw 4 may be formed with a generally cylindrical shape with one or more threads formed on a circumferential area thereof. The power screw 4 is configured to be rotatable relative to the nut 3 and the linear member 15. Additionally, the threads formed on the circumferential area of the power screw 3 may screwingly engage the threaded interior of the nut 3. As would be apparent to a person of ordinary skill in the art, the engagement of the threads of power screw 3 with the threaded interior of the nut 3 can translate rotation of the power screw 3 into linear movement of the nut 3, and the linear member 15 attached to the nut.

The power screw 4 may be formed from any material capable of conducting capacitance from a human user to a touch screen device in order to simulate the dielectric difference typically offered by a human appendage. Examples of potential materials for the power screw 4 include, but are not limited to natural or synthetic rubbers, plastic polymers (such as polypropylene), and metallic materials (such as aluminum). However, embodiments of the present application need not be required to conduct capacitance along their entire length and embodiments may include the conductive tip 1 being electrically isolated from the mouthpiece 6. Alternatively, the power screw 4 may be formed of any material, including the lightest materials available and/or non-conductive materials. In an embodiment of the mouth stylus having the power screw 4 formed from non-conductive materials, a conductor, such as a metallic wire may be provided to maintain the dielectric difference across the length of the stylus.

As discussed above, the linear member 15 may have an at least partially hollow interior configured to receive at least a portion of the power screw 4, as shown in FIG. 2 in some embodiments. In some embodiments, the linear member 15 may be configured to receive the entire power screw 4.

In the embodiments shown, the power screw 4 is shown as having a generally cylindrical shape with a threaded exterior that engages and is received within a hollow linear member 15. However, the power screw 4 and linear member 15 are not limited to this structure. For example, the power screw 4 may alternatively have a hollow, interior and the linear member 15 may have a threaded exterior that engages the threaded interior of the power screw 4 and is received within the power screw 4. Additionally, the power screw 4 and linear member 15 may have other alternative structures as would be apparent to a person of ordinary skill in the art.

The motor 5 is connected to an end of the power screw 4 and is configured to apply a torque to the power screw 4 to rotate the power screw 4 relative to nut 3 and the linear member 15. As discussed above, the threaded interior of the nut 3 engages the threaded exterior of the power screw 4 to translate the rotation of the power screw 4 into linear movement of the nut 3 and linear member 15. Thus, the torque applied to the power screw 4 by the motor 5 can be translated into linear movement of the linear member 15.

In some embodiments, the motor 5 may be a bi-directional rotary DC motor capable of rotating in both clockwise and counter-clockwise directions. In these embodiments, a battery and control logic 14 (shown in FIGS. 3-8) or other power source may be provided proximate to the motor. However, the motor 5 is not particularly limited to a bi-directional rotary DC motor, and may be any type of motor capable of applying a torque sufficient to rotate the power screw 4 relative to the nut 3 and linear member 15.

The mouthpiece 6 is connected to the motor 5 at an end of the motor 5 opposite the end of the motor 5 connected to the power screw 4. In some embodiments, the placement of the motor 5 may cause a weight imbalance along the length of the stylus such that the center of gravity of the stylus is biased toward the user's head. By biasing the center of gravity of the stylus closer to the user's head, the user may have easier control of the stylus. The mouthpiece 6 may be formed to have a shape and size that can be inserted into a user's mouth and be held in place by at least a portion of the mouth (i.e. at least one of the teeth, gums, lips, tongue, etc.) For example, the mouthpiece may have a generally u-shape, with upper and lower channels designed to receive a user's teeth. Other example embodiments of the mouthpiece may have different shapes capable of engaging a user's mouth as would be apparent to a person of ordinary skill in the art.

The mouthpiece 6 may be formed from any material safe for insertion into a human mouth and capable of conducting capacitance from a human user to a touch screen device in order to simulate the dielectric different typically offered by a human appendage. Examples of potential materials for the mouthpiece 6 may include, but are not limited to natural or synthetic rubbers, plastic polymers (such as polypropylene), and metallic materials. Additionally, the mouthpiece 6 may be configured to contact one of a user's lips, a user's gums, and a user's tongue to provide sufficient connection to conduct the user's capacitance to the conductive tip 1. However, embodiments of the present application need not be required to conduct capacitance along their entire length and embodiments may include the conductive tip 1 being electrically isolated from the mouthpiece 6. Alternatively, the mouthpiece 6 may be formed of any material, including the lightest materials available and/or non-conductive materials. In an embodiment of the mouth stylus having the mouthpiece 6 formed from non-conductive materials, a conductor, such as a metallic wire may be provided to maintain the dielectric difference across the length of the stylus.

One or more control mechanisms 7 and 8 may be integrated into the mouthpiece 6 to allow a user to control the rotation of the motor 5. As shown in FIG. 2, the control mechanisms 7 and 8 may comprise a pair of bite sensors 7 and 8 disposed on different sides of the mouthpiece 6, which control the direction of rotation of the motor 5 based on bite pressure measured at different portions of the mouth piece 6. For example, bite pressure may be sensed by a bite sensor 7 disposed on a right side (user's right) of the mouthpiece 6 and trigger rotation of the motor 5 in a first direction and bite pressure may be sensed by a bite sensor 8 disposed on a left side (user's left) of the mouthpiece 6 and trigger rotation of the motor in a second direction. Of course different embodiments may have the bite sensors 7 and 8 located at different locations. Further, in some embodiments application of bite pressure to both sensors simultaneously or substantially simultaneously may turn the motor off. Further, in some embodiments application of bite pressure to both sensors simultaneously or substantially simultaneously may turn the motor off. In some embodiments, the bite sensors 907 and 908 could trigger extension or retraction when a change in bite pressure is measured. Further, in some embodiments, the bite sensors 907 and 908 could trigger the extension or retraction when a change in bite pressure exceeds a threshold.

The bite sensors 7 and 8 may control the motor 5 by controlling the voltage applied from the battery or power source (14 in FIG. 3-8).

In this embodiment, a pair of control mechanisms 7 and 8 is provided in the form of two bite sensors. However, in different embodiments only a single control mechanism may be integrated into the mouthpiece 6. For Example, a paddle or switch may be integrated into the mouthpiece, which can be manipulated, with a tongue, in one direction to rotate the motor in a first direction, and manipulated in a different direction to rotate the motor in a second direction. Alternatively, the paddle or switch may be articulated in different directions by movement of the teeth or jaw in different directions or applying different biting pressures at different portions of the mouthpiece. In some embodiments, articulation of the paddle or switch with a tongue may be more advantageous than biting pressure sensors or jaw movement because the mouthpiece can be held firmly in place with constant uniform biting action to more accurately control the tip of the mouth stylus and the control mechanism articulated with the tongue.

FIGS. 3-8 show a second embodiment similar to the first embodiment discussed above. Many of the features of this second embodiment are similar to the features of the first embodiment discussed above. Thus, the same reference numerals are used for similar features between the embodiments, and redundant description is hereby omitted.

Figure 5:
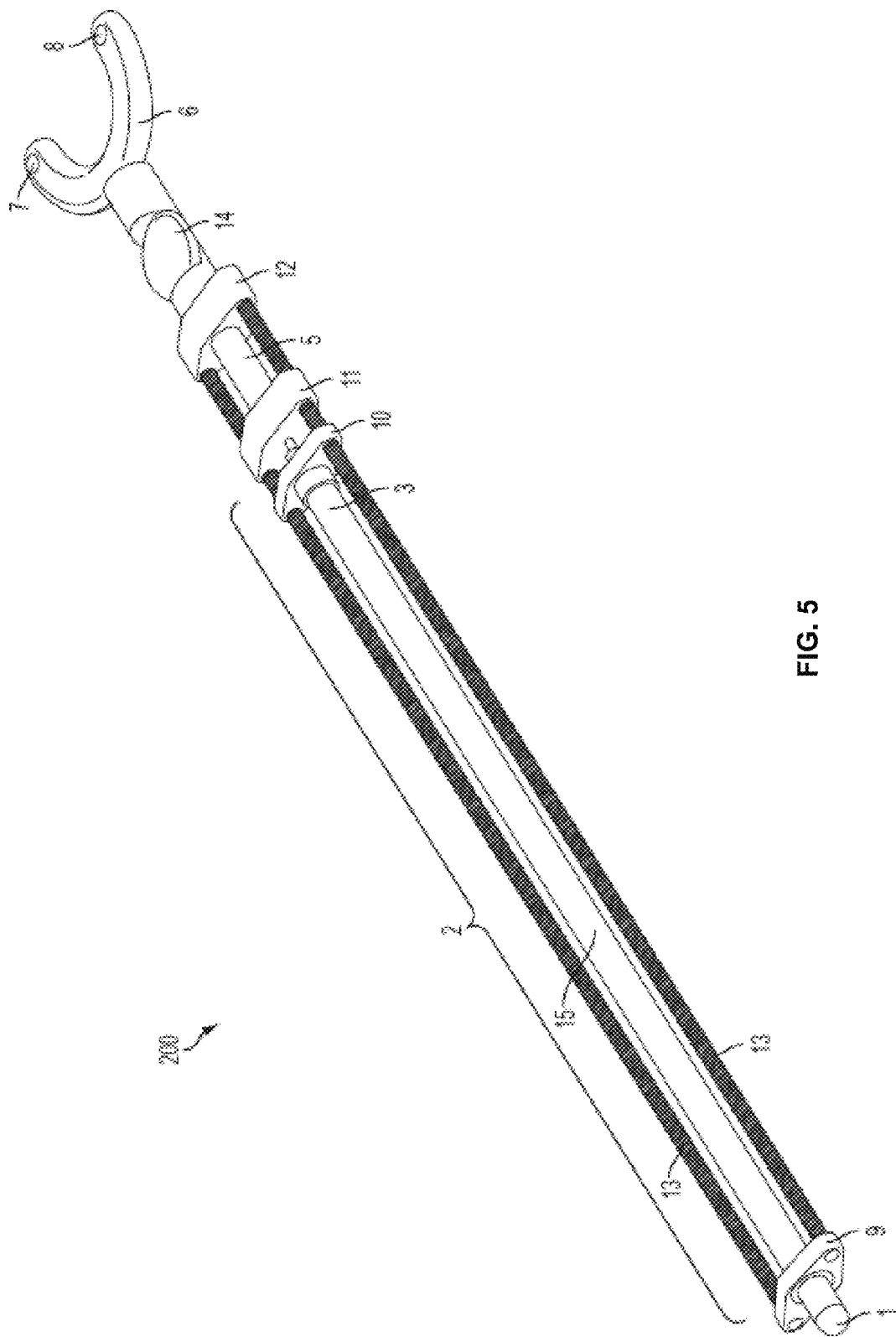
FIG. 5 is a perspective view diagram according to the second example embodiment of the extendable mouth stylus in the non-extended state
Figure 8:
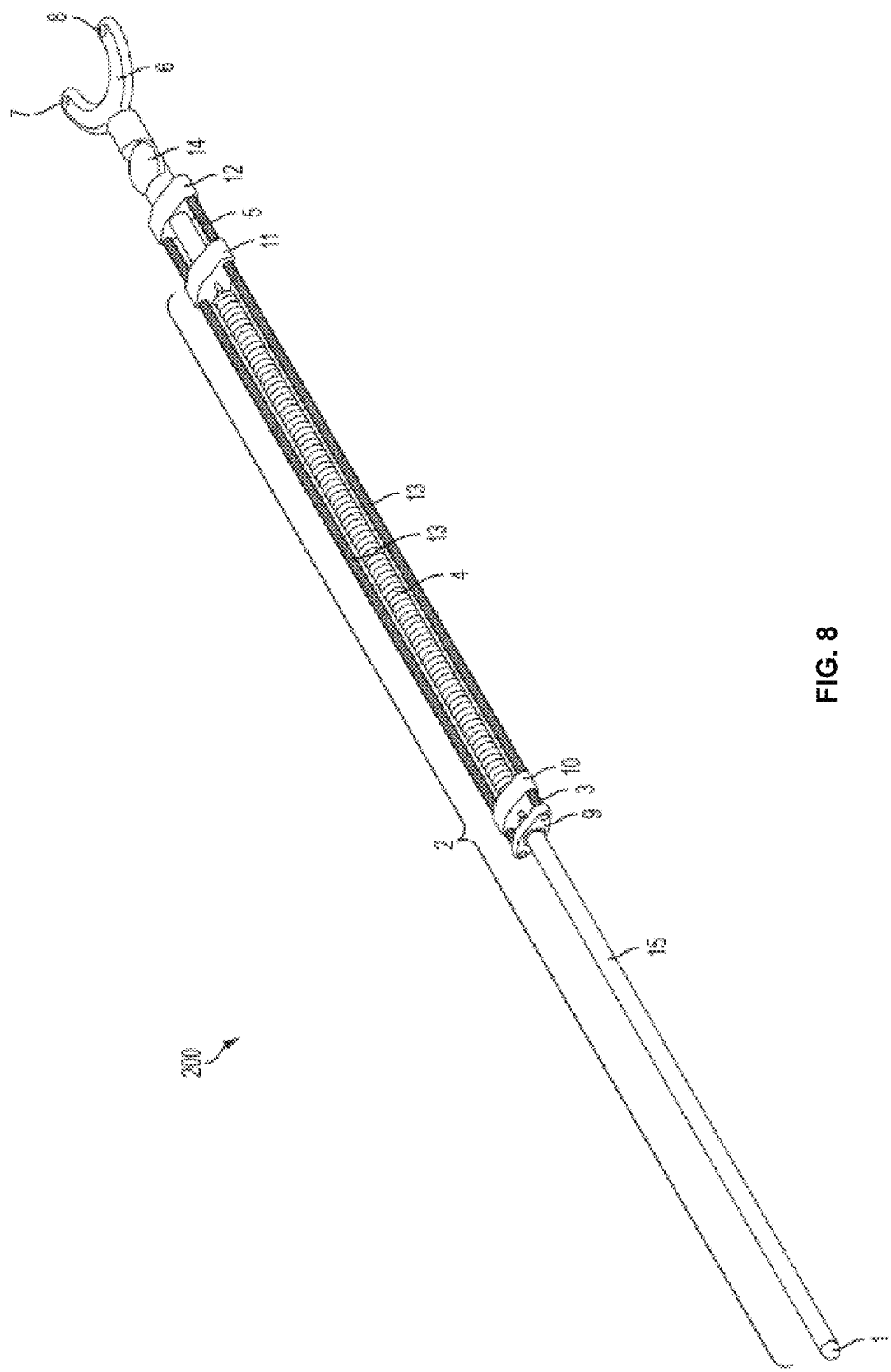
FIG. 8 is a perspective view diagram according to the second example embodiment of the extendable mouth stylus in the extended state.

FIGS. 3-5 show the second embodiment in a fully collapsed configuration with the power screw 4 retracted into the linear member 15. FIGS. 6-8 show the second embodiment in a fully extended configuration with the power screw 4 fully extended from the linear member 15.

In the embodiment shown in FIGS. 3-8, the stylus 200 includes a flexible, conductive tip 1, an extending portion 2, a mouthpiece 6, and a control mechanism(s) 7 and 8 integrated into the mouthpiece 6. As with the embodiment discussed above, the extending portion 2 includes a linear member 15, a nut 3 attached to the linear member 15, a power screw 4 rotatable relative to the nut 3 and the linear member 15, and a motor 5 disposed between the power screw 4 and the mouthpiece 6.

Additionally, the embodiment shown in FIGS. 3-8, the stylus 200 includes a pair of guide rails 13 disposed parallel to the extending portion 2. The guide rails 13 are connected to the stylus by a pair of motor frames 11, 12 and a pair of linear member frames 9, 10. Specifically, a first motor frame 11 is connected to the stylus 200 between the mouthpiece 6 and the motor 5. Additionally, a second motor frame 12 is connected to the stylus 200 between the motor 5 and the power screw 4.

The motor frames 11, 12 may be attached to the stylus 200 by various methods including adhesive, screw mounting, welding, pressure fitting, or any other method as would be apparent a person of ordinary skill in the art. The motor frames 11, 12 may also be fixed to the guide rails 13 such that the frames 11, 12 do not move relative to the guide rails 13.

Additionally, a first linear member frame 10 may be connected to the linear frame 15 at an end of the linear frame 15 proximate to the nut 3. The first linear member frame 10 may be attached to the linear member 15 by various methods including adhesive, screw mounting, welding, pressure fitting, or any other method as would be apparent a person of ordinary skill in the art. The first linear member frame 10 may also be fixed to the linear member 15 such that the first linear member frame 10 does not move relative to the linear member 15.

In some embodiments, the nut 3 may be integrated into the first linear frame 10. However, the nut 3 need not be integrated into the first linear frame 10 in some embodiments.

The first linear member frame 10 is configured to engage the guide rails 13 such that the first linear member frame 10 may move along the length of the guide rails 13. The guide rails 13 may contact the first linear member 10 in some embodiments. However, the guide rails 13 may not contact the first linear member frame 10 in some embodiments and may instead have a buffer space therebetween. In embodiments having a buffer space between the first linear member frame 10 and the guide rails 13, a conducting structure, such as a metallic brushing or a bridging wire may also be provided to maintain the dielectric difference across the length of the stylus.

Additionally, a second linear member frame 9 may be connected to the guide rails 13 proximate to the conductive tip 2, when the stylus is in a collapsed configuration shown in FIGS. 3-5. The second linear member frame 9 may be attached to the guide rails 13 by various methods including adhesive, screw mounting, welding, pressure fitting, or any other method as would be apparent a person of ordinary skill in the art. The second linear member frame 9 may also be fixed to the guide rails 13 such that the second linear member frame 9 does not move relative to the guide rails 13.

The second linear member frame 9 is configured to engage the linear member 15 such that the second linear member frame 9 may move along the length of the linear member 15. The linear member 15 may contact the second linear member 9 in some embodiments. However, the linear member 15 may not contact the second linear member frame 9 in some embodiments and may instead have a buffer space therebetween. In embodiments having a buffer space between the second linear member frame 9 and the linear member 15, a conducting structure, such as a metallic brushing or a bridging wire may also be provided to maintain the dielectric difference across the length of the stylus.

The combination of the motor frames 11, 12, the linear member frames 9, 10, and the guide rails 13 may be configured to prevent rotation of the linear member 15 relative to the motor 5.

The material construction of the motor frames 11, 12, linear member frames 9, 10, and the guide rails 13 is not particularly limited and may include, but is not limited to, one or more of natural or synthetic rubbers, plastic polymers (such as polypropylene), and metallic materials.

In this embodiment, two guide rails 13 were provided. However, other embodiments may include only a single guide rail, or may include three or more guide rails.

Figure 9:
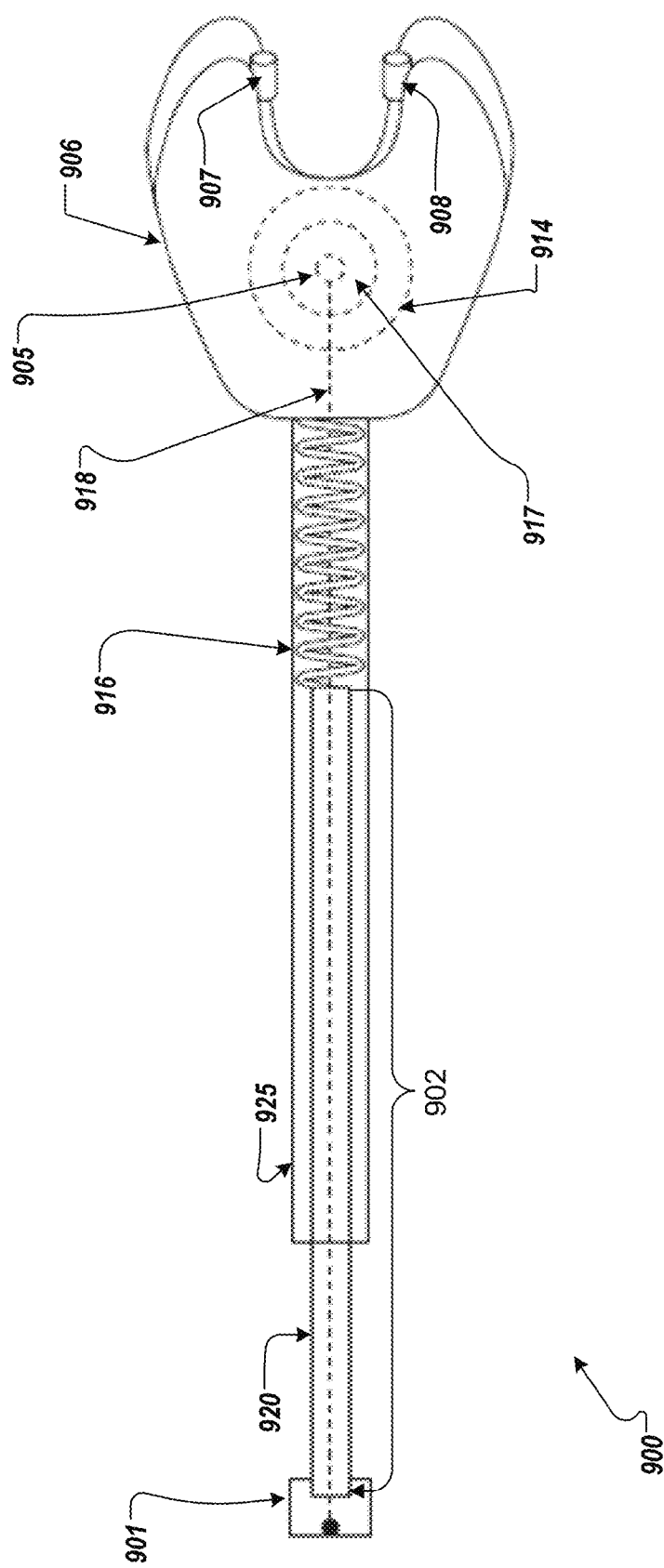
FIG. 9 is a top view diagram according to a third example embodiment of the extendable mouth stylus.

FIG. 9 shows a top view of a third embodiment of an extendable mouth stylus 900. Some of the features of this third embodiment are similar to the features of the first and second embodiments discussed above. Thus, the similar reference numerals are used for similar features between the embodiments, and redundant description is omitted. In the embodiment shown in FIG. 9, the stylus 900 includes a flexible, conductive tip 901, an extending portion 902, a motor 905, a mouthpiece 906, motor 905 and control mechanisms 907 and 908 integrated into the mouthpiece 906. However, in this embodiment, the extending portion 902 has no linear member, nut, or power screw as was present in the first and second embodiments. Instead, the extending portion 902 may be formed from a plurality of linear pieces, such as the first linear piece 920 and the second linear piece 925 illustrated in FIG. 9. Further, the first linear piece 920 may be shaped and sized to slide into a hollow portion of the second linear piece 925 telescopically as illustrated in FIG. 9. In the embodiment shown in FIG. 9 the extending portion 902 is formed by two linear pieces 920, 925, but embodiments of the present application are not limited to only two linear pieces may include any number of linear pieces. Further, the arrangement of telescoping parts may be reversed such that the second linear piece 925 slides into the first linear piece.

The first linear piece 920 may be formed as a generally cylindrical shaft, with the conductive tip 901 attached at one end. However, the linear piece 920 is not limited to a generally cylindrical shape, and may have any shape as would be apparent to a person of ordinary skill in the art. The conductive tip 901 may be attached by various methods including, but not limited to adhesive attachment, a threaded screw, welding, press fitting or any other attachment method apparent to a person of ordinary skill in the art.

The first linear piece 920 may be formed from any material capable of conducting capacitance from a human user to a touch screen device in order to simulate the dielectric difference typically offered by a human appendage. Examples of potential materials for the first linear piece 920 include, but are not limited to natural or synthetic rubbers, plastic polymers (such as polypropylene), and metallic materials (such as aluminum). However, embodiments of the present application need not be required to conduct capacitance along their entire length and embodiments may include the conductive tip 901 being electrically isolated from the mouthpiece 906. Alternatively, the first linear piece 920 may be formed of any material, including the lightest materials available and/or non-conductive materials. In an embodiment of the mouth stylus having the first linear piece 920 formed from non-conductive materials, a conductor, such as a metallic wire may be provided to maintain the dielectric difference across the length of the stylus.

Further, the second linear piece 925 may also be formed as a generally cylindrical shaft attached to the mouthpiece 906 at one end. However, the second linear piece 925 is not limited to a generally cylindrical shape, and may have any shape as would be apparent to a person of ordinary skill in the art. The second linear piece 925 may be attached to the mouthpiece 906 by a variety of methods including, but not limited to adhesive attachment, a threaded screw, welding, press fitting or any other attachment method apparent to a person of ordinary skill in the art.

The second linear piece 925 may be formed from any material capable of conducting capacitance from a human user to a touch screen device in order to simulate the dielectric difference typically offered by a human appendage. Examples of potential materials for the second linear piece 925 include, but are not limited to natural or synthetic rubbers, plastic polymers (such as polypropylene), and metallic materials (such as aluminum). However, embodiments of the present application need not be required to conduct capacitance along their entire length and embodiments may include the conductive tip 901 being electrically isolated from the mouthpiece 906. Alternatively, the second linear piece 925 may be formed of any material, including the lightest materials available and/or non-conductive materials. In an embodiment of the mouth stylus having the second linear piece 925 formed from non-conductive materials, a conductor, such as a metallic wire may be provided to maintain the dielectric difference across the length of the stylus.

Additionally, a biasing member 916 may be provided within the second linear piece 925 to provide a biasing force to the first linear piece 920 and bias the first linear piece 920 toward an extended position extending the conductive tip 901 away from the mouthpiece 906. The biasing member 916 may be a linear spring or any other type of biasing member that may be apparent to a person of ordinary skill in the art. The tensioning member is otherwise not particularly limited and may be formed from any material as may be apparent to a person of ordinary skill in the art.

A tensioning member 918 also be within the second linear piece 925 and may be connected to the first linear piece 920 and provide a tensioning force to balance and counteract the biasing force provided by the biasing member 916 discussed above. The tensioning member 918 may be a string, thread, wire, linear fiber, or any other structure that may be apparent to a person of ordinary skill in the art. The tensioning member 918 may be attached to the first linear member 920 by various methods including, but not limited to adhesive attachment, a threaded screw, welding, press fitting or any other attachment method apparent to a person of ordinary skill in the art.

The tensioning member 918 may be connected to and wound around a spool 917 disposed within the mouthpiece 906 and be threaded through hollow portions of the biasing member 916 and the second linear piece 920. The tensioning member 918 may also be threaded through a hollow portion of the first linear member 920 so as to connect to the first linear member at a position proximate to the conductive tip 901. However, embodiments of the present application need not have the tensioning member threaded through hollow portions of the biasing member 916, or first and second hollow portions 920, 925. The tensioning member is otherwise not particularly limited and may be formed from any material as may be apparent to a person of ordinary skill in the art.

The spool 917 is disposed within or proximate to the mouthpiece 906 and is connected to the motor 905 so as to rotatable by the motor 905. The spool 917 is not particularly limited and may be formed from any material as may be apparent to a person of ordinary skill in the art.

The motor 905 is configured to apply a torque to the spool 917 to rotate the spool 917 and cause the tensioning member 918 to be wound and unwound from the spool 917. As discussed above, the tensioning member 918 provides a tensioning force to the first linear piece 920 to counter balance the biasing force provided by the biasing member 916. Thus, as the tensioning member 918 is unwound from the spool 917, the tensioning force decreases and the biasing force causes the first linear piece 920 to move linearly away from the mouth piece 906 and the length of the extending portion 902 increases. Conversely, as the tensioning member 918 is wound around the spool 917, the tensioning force increases causing the first linear piece 920 to move toward the mouth piece 906 and the length of the extending portion 902 decreases.

In some embodiments, the motor 905 may be a bi-directional rotary DC motor capable of rotating in both clockwise and counter-clockwise directions. In these embodiments, a battery 914, and optionally control logic, or other power source may be provided proximate to the motor. However, the motor 905 is not particularly limited to a bi-directional rotary DC motor, and may be any type of motor capable of applying a torque sufficient to rotate the spool 917 to wind and unwind the biasing member.

The motor 905 may be disposed within the mouthpiece 906. However, embodiments of the present application are not limited to this configuration and may have other configurations. For example, the motor 905 may be connected to the mouthpiece 906 at an end of the motor 905 opposite the end of the motor 905 connected to the spool 917. In some embodiments, the placement of the motor 905 may cause a weight imbalance along the length of the stylus such that the center of gravity of the stylus is biased toward the user's head. By biasing the center of gravity of the stylus closer to the user's head, the user may have easier control of the stylus.

The mouthpiece 906 may be formed to have a shape and size that can be inserted into a user's mouth and be held in place by at least a portion of the mouth (i.e. at least one of the teeth, gums, lips, tongue, etc.) For example, the mouthpiece 906 may have a generally u-shape, with upper and lower channels designed to receive a user's teeth. Other example embodiments of the mouthpiece may have different shapes capable of engaging a user's mouth as would be apparent to a person of ordinary skill in the art.

The mouthpiece 906 may be formed from any material safe for insertion into a human mouth and capable of conducting capacitance from a human user to a touch screen device in order to simulate the dielectric different typically offered by a human appendage. Examples of potential materials for the mouthpiece 906 may include, but are not limited to natural or synthetic rubbers, plastic polymers (such as polypropylene), and metallic materials. Additionally, the mouthpiece 906 may be configured to contact one of a user's lips, a user's gums, and a user's tongue to provide sufficient connection to conduct the user's capacitance to the conductive tip 901. However, embodiments of the present application need not be required to conduct capacitance along their entire length and embodiments may include the conductive tip 901 being electrically isolated from the mouthpiece 906.

Alternatively, the mouthpiece 906 may be formed of any material, including the lightest materials available and/or non-conductive materials. In an embodiment of the mouth stylus having the mouthpiece 906 formed from non-conductive materials, a conductor, such as a metallic wire may be provided to maintain the dielectric difference across the length of the stylus.

One or more control mechanisms 907 and 908 may be integrated into the mouthpiece 906 to allow a user to control the rotation of the motor 905 and spool 907 to wind and/or unwind the tensioning member 918. As shown in FIG. 9, the control mechanisms 907 and 908 may comprise a pair of bite sensors 907 and 908 disposed on different sides of the mouthpiece 906, which to control the direction of rotation of the motor 905 based on a bite pressure measured at different portions of the mouthpiece 906. For example, bite pressure may be sensed by a bite sensor 907 disposed on a right side (user's right) of the mouthpiece 906 and trigger rotation of the motor 905 and spool 917 in a first direction to unwind the tensioning member 918 and bite pressure may be sensed by a bite sensor 908 disposed on a left side (user's left) of the mouthpiece 906 and trigger rotation of the motor 905 and spool 917 in a second direction to wind the tensioning member 918 clockwise. Of course different embodiments may have the bite sensors 907 and 908 located at different locations. Further, in some embodiments application of bite pressure to both sensors simultaneously or substantially simultaneously may turn the motor off. In some embodiments, the bite sensors 907 and 908 could trigger extension or retraction when a change in bite pressure is measured. Further, in some embodiments, the bite sensors 907 and 908 could trigger the extension or retraction when a change in bite pressure exceeds a threshold.

The bite sensors 907 and 908 may control the motor 905 by controlling the voltage applied from the battery or power source 914. Additionally, in some embodiments control logic or other circuitry for controlling the motor 905 may also be provided proximate to the battery or power source 914.

In this embodiment, a pair of control mechanisms 907 and 908 is provided in the form of two bite sensors. However, in different embodiments only a single control mechanism may be integrated into the mouthpiece 906. For example, a paddle or switch may be integrated into the mouthpiece, which can be manipulated, with a tongue, in one direction to rotate the motor clockwise, and manipulated in a different direction to rotate the motor counter-clockwise. Alternatively, the paddle or switch may be manipulated in different directions by movement of the teeth or jaw in different directions or applying different biting pressures at different portions of the mouthpiece. In some embodiments, articulation of the paddle or switch with a tongue may be more advantageous than biting pressure sensors or jaw movement because the mouthpiece can be held firmly in place with constant uniform biting action to more accurately control the tip of the mouth stylus and the control mechanism articulated with the tongue.

Mechanically Extendable Mouth Stylus

Figure 10:
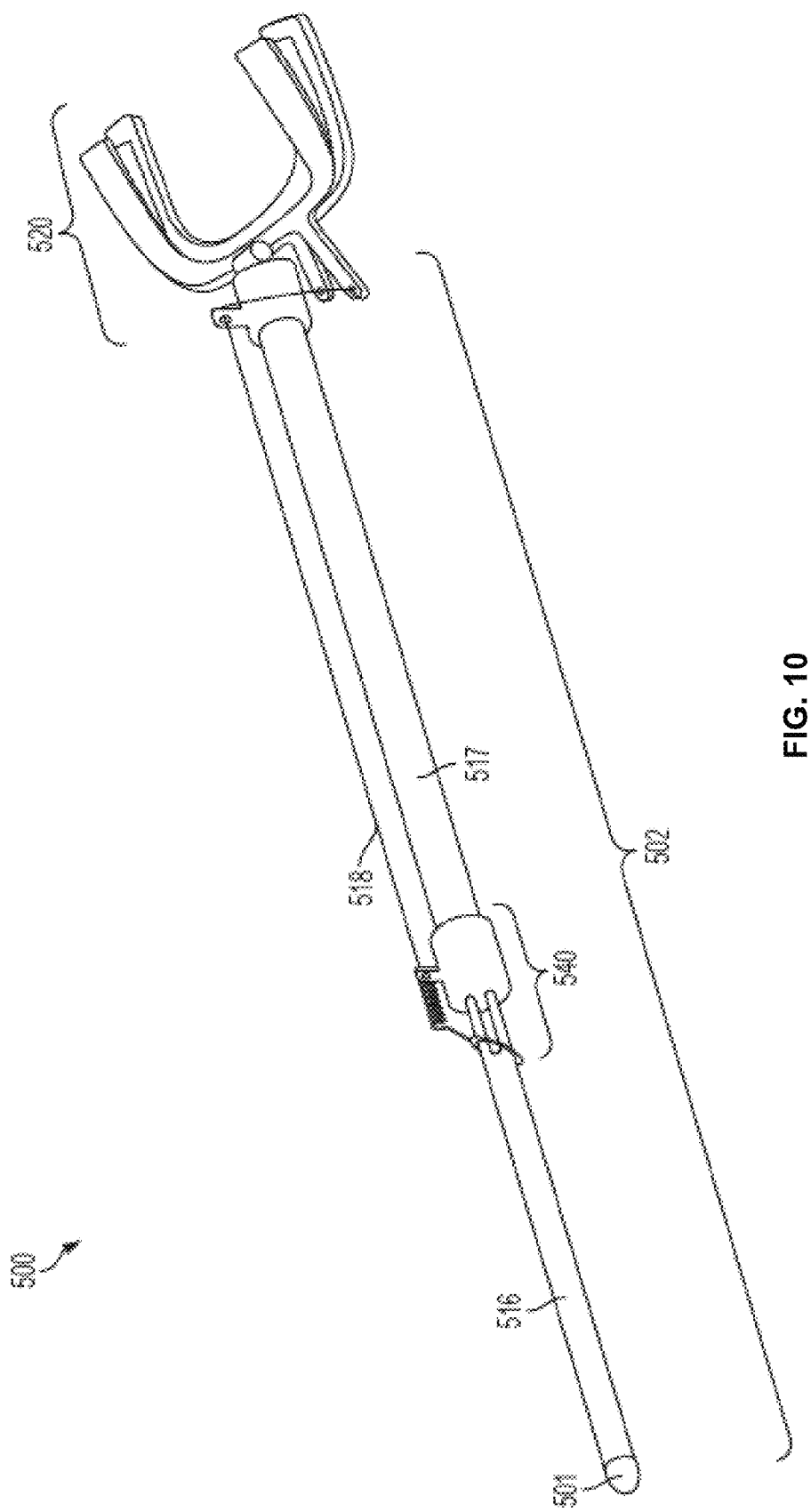
FIG. 10 is a perspective view diagram according to a fourth example embodiment of the extendable mouth stylus.
Figure 11:
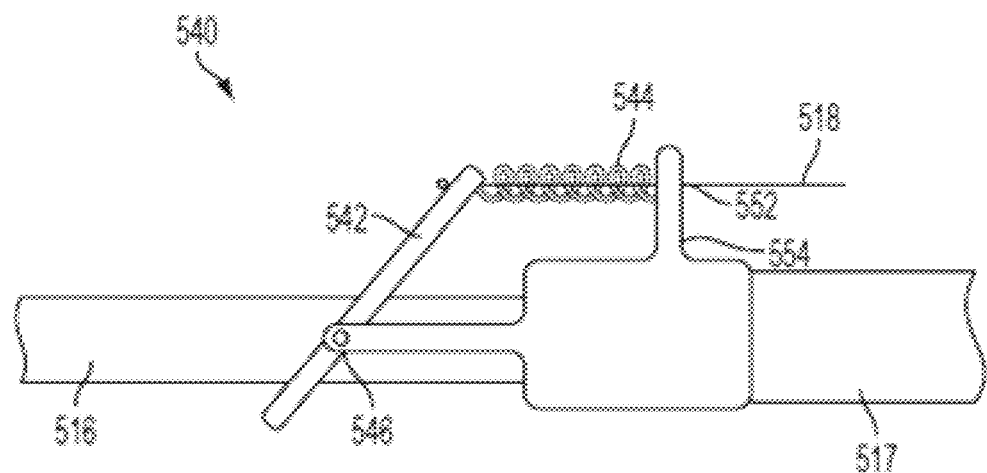
FIG. 11 is an enlarged portion of a locking mechanism according to the fourth example embodiment of the extendable mouth stylus.
Figure 12:
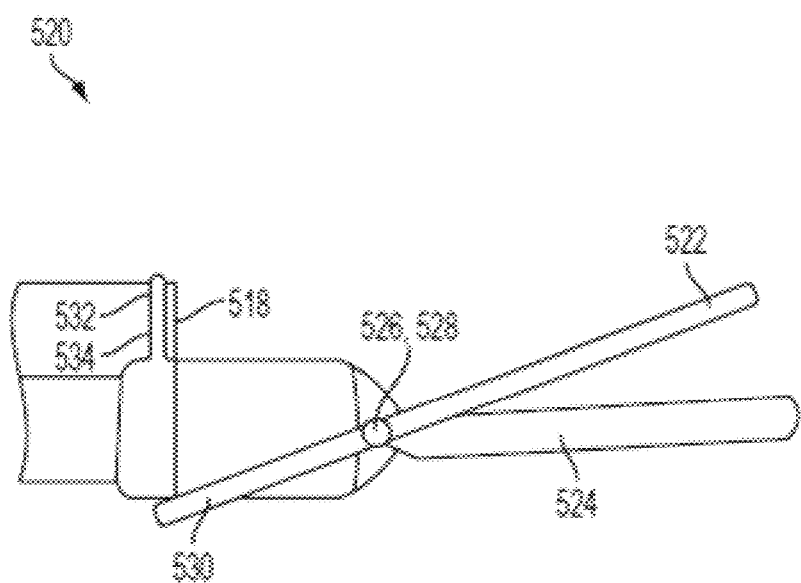
FIG. 12 is an enlarged portion of a mouthpiece assembly according to the fourth example embodiment of the extendable mouth stylus.
Figure 13:
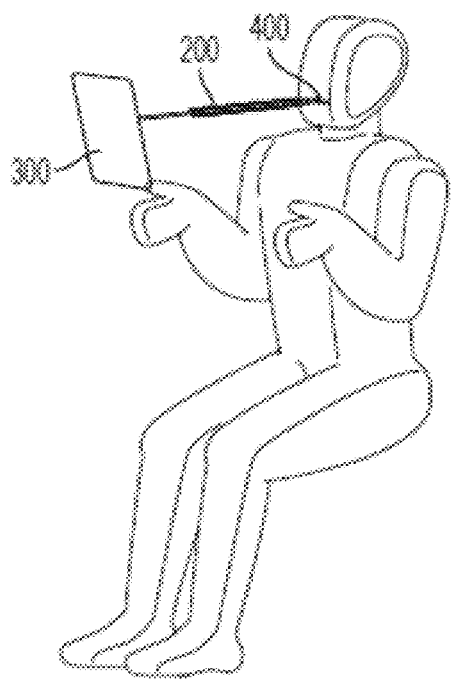
FIG. 13 is a perspective, front view diagram of a user using an embodiment of the extendable mouth stylus.
Figure 14:
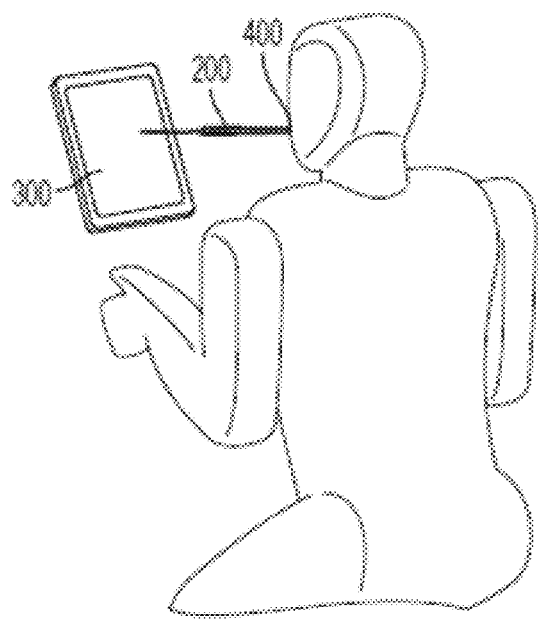
FIG. 14 is a perspective, over shoulder view diagram of a user using an embodiment of the extendable mouth stylus.
Figure 15:
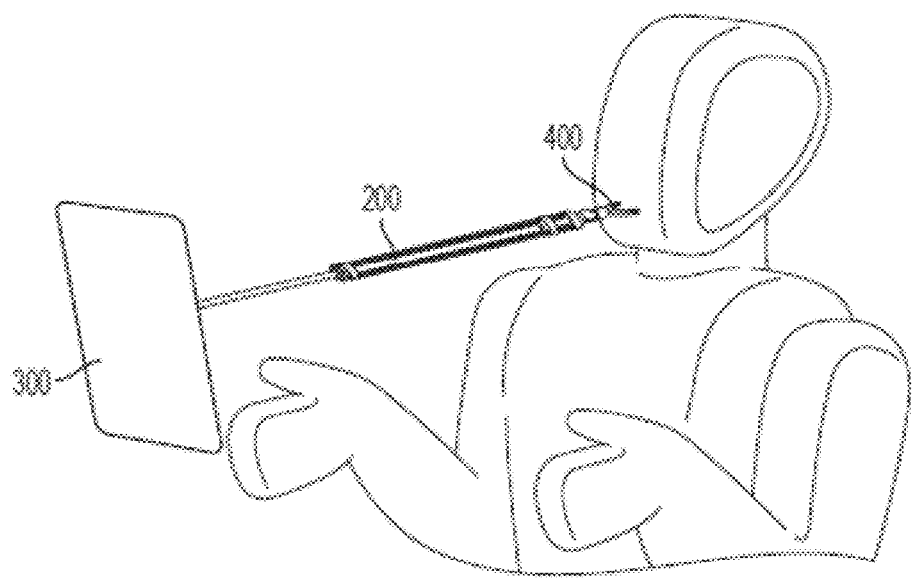
FIG. 15 is an enlarged perspective, front view diagram of a user using an embodiment of the extendable mouth stylus.
Figure 16:
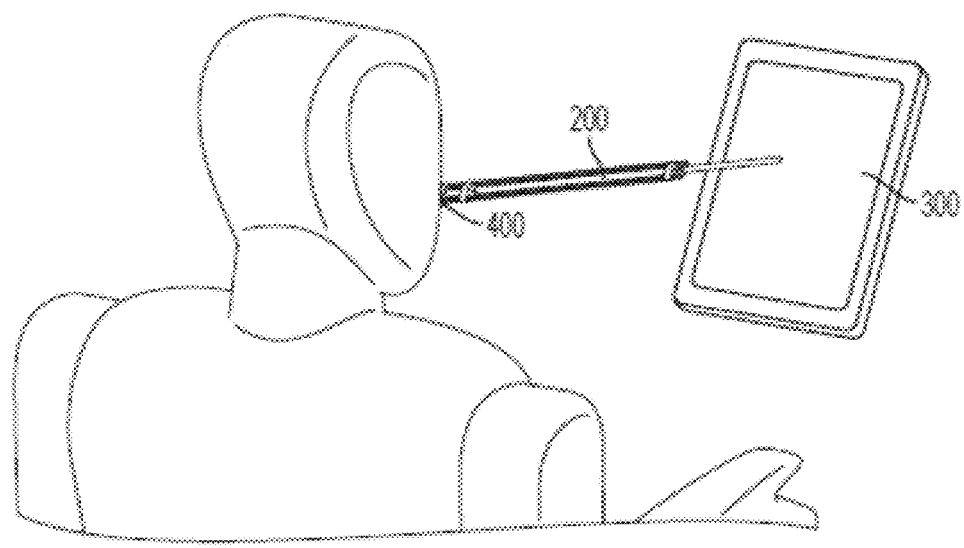
FIG. 16 is an enlarged perspective, over shoulder view diagram of a user using an embodiment of the extendable mouth stylus.

FIGS. 10-12 show a fourth embodiment of an extendable mouth stylus 500. In this embodiment, the extension of the mouth stylus is controlled mechanically, rather than electromechanically as done in the above discussed embodiments. Some of the features of the present embodiment are similar to features of the embodiments discussed above such that similar reference numerals are used for similar features between the embodiments, and redundant description is hereby omitted.

FIG. 10 illustrates a perspective view diagram of the fourth example embodiment of the extendable mouth stylus 500. The extendable mouth stylus 500 includes a flexible tip 501, an extending portion 502, and a mouthpiece assembly 520, which is configured to mechanically control the extending portion 502 via a string 518 extending along at least a part of the length of the extending portion. In this embodiment, the extending portion 502 includes a movable portion 516, a stationary portion 517, a locking mechanism 540 connecting the movable portion 516 and the stationary portion 517.

Like the conductive tip 1 of the first and second embodiments discussed above, the conductive tip 501 may be formed from a material capable of conducting capacitance from a human user to a touch screen device in order to simulate the dielectric difference typically offered by a human appendage. In other words, the stylus may be capable of conducting capacitance along its entire length between the user and the touch screen device so that the dielectric difference necessary to operate the capacitive screens can be maintained. Examples of potential materials for the conductive tip 1 include, but are not limited to natural or synthetic rubbers, plastic polymers (such as polypropylene), and metallic materials (such as aluminum). However, embodiments of the present application need not be required to conduct capacitance along their entire length and embodiments may include the conductive tip 1 being electrically isolated from the mouthpiece 6.

Similar to the conductive tip 1, the conductive tip 501 may be formed to have a hemi-spherical or dome shape, but is not particularly limited to this shape. Alternatively, the tip may be formed to have a cylindrical shape, a conical shape, or any other shape apparent to a person of ordinary skill in the art. In some embodiments, the conductive tip 501 may be formed to have a diameter equal to or greater than one-quarter (0.25) inch. However, the tip is not specifically limited to this size and could have any size selected by a person of ordinary skill in the art.

As discussed above, in this embodiment, the extending portion 502 includes a movable portion 516, a stationary portion 517, a locking mechanism 540 connecting the movable portion 516 and the stationary portion 517. The movable portion 516 may be formed as a generally cylindrical shaft, with the conductive tip 501 attached at one end. However, the movable portion 516 is not limited to a generally cylindrical shape, and may have any shape as would be apparent to a person of ordinary skill in the art. The conductive tip 501 may be attached by various methods including, but not limited to adhesive attachment, a threaded screw, welding, press fitting or any other attachment method apparent to a person of ordinary skill in the art.

Similarly, the stationary portion 517 may be formed as a generally cylindrical shaft, with the mouthpiece assembly 520 attached at one end. However, the stationary portion 517 is not limited to a generally cylindrical shape, and may have any shape as would be apparent to a person of ordinary skill in the art. The mouthpiece assembly 520 may be attached by various methods including, but not limited to adhesive attachment, a threaded screw, welding, press fitting or any other attachment method apparent to a person of ordinary skill in the art.

In some embodiments, the stationary portion 517 may have an at least partially hollow interior configured to receive at least a portion of the movable portion 416 therein. However, the stationary portion 517 is not required to be hollow, nor is it required to receive any portion of the movable portion 516. The stationary member 517 and the movable portion 516 may be formed from any material capable of conducting capacitance from a human user to a touch screen device in order to simulate the dielectric difference typically offered by a human appendage. Examples of potential materials for the stationary member 517 and the movable portion 516 may include, but are not limited to natural or synthetic rubbers, plastic polymers (such as polypropylene), and metallic materials (such as aluminum). However, embodiments of the present application need not be required to conduct capacitance along their entire length and embodiments may include the conductive tip 501 being electrically isolated from the mouthpiece assembly 520. Alternatively, the stationary member 517 and the movable portion 516 may be formed of any material, including the lightest materials available and/or non-conductive materials. In an embodiment of the mouth stylus having the stationary member 517 and the movable portion 516 formed from non-conductive materials, a conductor, such as a metallic wire may be provided to maintain the dielectric difference across the length of the stylus.

The locking mechanism 540 may connect the stationary member 517 and the movable member 516 such that the movable member 516 can move linearly relative to the stationary member 517. Further, the locking mechanism 540 may be configured to be controlled by the mouthpiece assembly 520 through the string 518 to hold the movable member 516 at a fixed length. FIG. 11 provides an enlarged view of the locking mechanism 540.

As illustrated in FIG. 11, the locking mechanism 540 includes a locking ring 542, a compressed spring 544, a revolute joint 546, an extending fin 554 having a through-hole 552 formed there through. As shown in the FIG. 11, the movable portion 516 and the stationary portion 517 are linearly connected, with the locking mechanism disposed therebetween. The movable portion 516 is inserted through the locking ring 542, which is connected to the locking mechanism 540 by the revolute joint 546. Further, the string 518 is inserted through the through-hole 552, along an axis of the spring 544 and connected to the locking ring 542, such that tension applied to the string 518 compresses the spring 544 and rotates the locking ring 542 about the revolute joint 546 applying a friction force to the movable portion 516 to prevent movement of the movable portion 516 relative to the stationary portion 517. Alternatively, when no tension is applied to string 518, the spring 544 un-compresses, rotating the locking ring 542 about the revolute joint 546, reducing or removing the friction force between the locking ring 542 and the movable portion 516 and allowing the movable portion 516 to move relative to the stationary portion 517.

The tension applied to the string 518 is controlled by a user through the mouthpiece assembly 520. FIG. 12 provides an enlarged view of the mouthpiece assembly 520.

As illustrated, the mouthpiece assembly 520 has a fixed lower portion 524 and articulating upper portion 522 which articulates about a revolute joint 526 containing a torsion spring 528. The torsion spring 528 acts to keep the upper portion 522 and lower portion 524 separated by a maximum gap of approximately one-half (0.5) inch. A lever arm 530 is attached to the articulating upper portion 522 of the mouthpiece assembly 520. The lever arm 530 is attached to the string 518, passing through a through-hole 534 formed through a fin 534 formed on the mouthpiece assembly. The string 518 is then routed down the length of the stationary portion 517 to the locking mechanism 540. As discussed above, the string 518 passes through the center of the compression spring 544 and attaches to the locking ring 542. Thus, the string 518 pulls on locking ring 542 to keep the locking ring 542 engaged with the extending portion, thereby keeping the extending portion temporarily fixed.

When a bite force is applied to the articulating upper portion 522 of the mouthpiece assembly 520, the torsion spring 528 is easily overcome and the string 518 is relaxed by way of the lever arm 530 moving vertically upward. As the string 518 is relaxed sufficiently, the compression spring 544 in the locking mechanism 540 tends to expand, thereby pushing on the upper end of the locking ring 542. The locking ring 542 rotates counterclockwise in reaction to the spring force, rotating about its own revolute joint 546, ultimately disengaging the extending portion 516. With the locking ring 542 disengaged from the movable portion 516, the movable portion 516 is free to translate in or out, whether by gravitational force or by air pressure supplied by the user's lungs and channeled through the center of the stationary portion 517.

When the bite force is again removed, the articulating upper portion 522 of the mouthpiece assembly 520 returns to its original position under influence of the torsion spring 528, which causes the lever arm 530 to pull back on the string 518. The retracting string 518 pulls on the locking ring 542 causing it to overcome the compression spring 544 and eventually re-engaging the movable portion 516, temporarily fixing the movable portion's 516 position.

The components of the mouthpiece assembly 520 may be formed from any material safe for insertion into a human mouth and capable of conducting capacitance from a human user to a touch screen device in order to simulate the dielectric different typically offered by a human appendage. Examples of potential materials for the components of the mouthpiece assembly 520 may include, but are not limited to natural or synthetic rubbers, plastic polymers (such as polypropylene), and metallic materials. Additionally, the components of the mouthpiece assembly 520 may be configured to contact one of a user's lips, a user's gums, and a user's tongue to provide sufficient connection to conduct the user's capacitance to the conductive tip 501. However, embodiments of the present application need not be required to conduct capacitance along their entire length and embodiments may include the conductive tip 501 being electrically isolated from the mouthpiece assembly 520. Alternatively, the components of the mouthpiece assembly 520 may be formed of any material, including the lightest materials available and/or non-conductive materials. In an embodiment of the mouth stylus having the components of the mouthpiece assembly 520 formed from non-conductive materials, a conductor, such as a metallic wire may be provided to maintain the dielectric difference across the length of the stylus.

The components of the locking mechanism 540 may be formed from any material capable of conducting capacitance from a human user to a touch screen device in order to simulate the dielectric difference typically offered by a human appendage. Examples of potential materials for the components of the locking mechanism 540 include, but are not limited to natural or synthetic rubbers, plastic polymers (such as polypropylene), and metallic materials (such as aluminum). However, embodiments of the present application need not be required to conduct capacitance along their entire length and embodiments may include the conductive tip 501 being electrically isolated from the mouthpiece assembly 520. Alternatively, the components of the locking mechanism 540 may be formed of any material, including the lightest materials available and/or non-conductive materials. In an embodiment of the mouth stylus having the components of the locking mechanism 540 formed from non-conductive materials, a conductor, such as a metallic wire may be provided to maintain the dielectric difference across the length of the stylus.

Mouth Stylus Operation

FIGS. 13-16 show various angles of the operation of a mouth stylus by a user. Specifically, a mouth stylus 200 being used by a user 400 to operate a touch screen device 300. The stylus 200 is similar to the embodiment shown in FIGS. 3-8. Of course alternative embodiments of the extendable stylus could be used. The stylus 200 is inserted into the user's 400 mouth and the user 400 can manipulate the stylus 200 to activate icons or items displayed on the touch screen device 300 using a combination of jaw muscles, oral muscles, facial muscles and neck muscles. Additionally, the user can extend and retract the length of the stylus using the various control means discussed above. For example, extension and retraction of the stylus 200 may be controlled through bite sensors integrated at different portions of the mouthpiece or a tongue paddle integrated into the mouthpiece.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly not limited.

For example, in some embodiments, a miniature laser range finder could be incorporated into the stylus and could be used to measure the distance between the user and the mobile device. In such embodiments, a logic processor could be incorporated into the stylus to automatically extend or retract the extendable portion based on the distance measured by the range finder.

Further, in other embodiments the control mechanism could include an optical system incorporated into the mouthpiece. For example, an IR sensor could be provided in the mouthpiece and an IR sensor, when covered or obscured by a tongue or some other part of the mouth, could trigger extension or retraction of the stylus. In some embodiments, the IR sensor could trigger extension or retraction when a change in measured IR radiation is measured. Further, in some embodiments, the IR sensor could trigger the extension or retraction when a change in measured IR radiation exceeds a threshold.

Further, in other embodiments, the control mechanism could include a wireless receiver (for example, a Bluetooth receiver) in communication with a wireless transmitting device (for example, a Bluetooth control device such as a track pad). In such embodiments, the extension and retraction of the stylus may be controlled via a Bluetooth connection to a track pad (or some other Bluetooth control device) if the user has residual finger control.

Further, in other embodiments, the control mechanism could include one or more sensors that measure airflow within or through the mouthpiece. For example, in such an embodiment, the one or more sensors could measure of direction of air flow to determine if a user is "sucking" air in, or "blowing" air out. In such embodiments, the sensors can initiate extension and retraction of the stylus by detection of "sucking" and "blowing" by the user. In some embodiments, the one or more sensors could trigger extension or retraction when a change in direction of air flow is measured. Further, in some embodiments, the one or more sensors could trigger extension or retraction when an air flow measured exceeds a threshold.

Further embodiments may include the control mechanism being removably connected to the mouthpiece such that the control mechanism of one embodiment may be removed and replaced with a control mechanism of another embodiment. For example, a control mechanism using pressure sensitive bite sensors may be removably connected or integrated into the mouth piece such that the bite sensors can be replaced with optical tongue sensors or air flow sensors based on the capabilities of the user.

Further, in the above discussed embodiments, a conductive tip is provided at the end of the stylus. However, embodiments of the present application are not limited to having a conductive tip and may include tips formed from non-conductive material. For example, a non-conductive paint-brush tip may be attached to the end of the stylus to allow a user to paint. Additionally, the conductive tip and/or the non-conductive tip may be removably connected to the stylus such that the tip can be removed and replaced based on the intended use of the user.

Thus, it is to be understood that the description and drawings presented herein represent a present embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly not limited.

The invention claimed is:

1. An extendable stylus configured to be operated with a mouth, the extendable stylus comprising:
    an extending portion configured to have an adjustable length, the extending portion comprising:
        a linear portion having the conductive tip connected to a first end thereof;
        a nut disposed at a second end of the linear portion opposite the first end;
        a power screw, which screwingly engages the nut disposed at the second end of the linear portion, wherein the power screw is rotatable relative to the nut and linear portion; and a motor configured to rotate the power screw relative to the nut and the linear portion;
a conductive tip configured to interface with a touch screen device, wherein the conductive tip is disposed at a first end of the extending portion;
a mouthpiece configured to engage the mouth of a user, wherein the mouthpiece is disposed at a second end of the extending portion, opposite the first end; and
a control mechanism configured to control the length of the extending portion based on an operation by the mouth of the user and disposed proximate to the second end of the extending portion, the control mechanism comprising:
a first bite sensor disposed in a first portion of the mouthpiece and a second bite sensor disposed in a second portion of the mouthpiece,
wherein the first bite sensor is configured to cause the motor to rotate in a first angular direction in response to sensing a pressure in the first portion of the mouthpiece and the second bite sensor is configured to cause the motor to rotate in a second angular direction in response to sensing a pressure in the second portion of the mouthpiece.

2. The extendable stylus according to claim 1 further comprising at least one guide rail connected to the motor at a first end of the guide rail and connected at a second end of the guide rail to a frame, wherein the frame is configured to allow the linear member to move linearly relative to the frame and is also configured to prevent rotation of the linear member relative to motor.

3. An extendable stylus configured to be operated with a mouth, the extendable stylus comprising:
an extending portion configured to have an adjustable length, the extending portion comprising:
a linear portion having the conductive tip connected to a first end thereof;
a nut disposed at a second end of the linear portion opposite the first end;
a power screw, which screwingly engages the nut disposed at the second end of the linear portion, wherein the power screw is rotatable relative to the nut and linear portion; and
a motor configured to rotate the power screw relative to the nut and the linear portion;
a conductive tip configured to interface with a touch screen device, wherein the conductive tip is disposed at a first end of the extending portion;
a mouthpiece configured to engage the mouth of a user, wherein the mouthpiece is disposed at a second end of the extending portion, opposite the first end; and
a control mechanism configured to control the length of the extending portion based on an operation by the mouth of the user and disposed proximate to the second end of the extending portion, the control mechanism comprising:
a tongue paddle connected to a first portion of the mouthpiece;
wherein the tongue paddle is configured to cause the motor to rotate in a first angular direction when the tongue paddle is manipulated in a first direction; and
wherein the tongue paddle is configured to cause the motor to rotate in a second angular direction when the tongue paddle is manipulated in a second direction different from the first direction.

4. An extendable stylus configured to be operated with a mouth, the extendable stylus comprising:
an extending portion configured to have an adjustable length, the extending portion comprising:
a linear portion having the conductive tip connected to a first end thereof;
a nut disposed at a second end of the linear portion opposite the first end;
a power screw, which screwingly engages the nut disposed at the second end of the linear portion, wherein the power screw is rotatable relative to the nut and linear portion; and
a motor configured to rotate the power screw relative to the nut and the linear portion;
a conductive tip configured to interface with a touch screen device, wherein the conductive tip is disposed at a first end of the extending portion;
a mouthpiece configured to engage the mouth of a user, wherein the mouthpiece is disposed at a second end of the extending portion, opposite the first end; and
a control mechanism configured to control the length of the extending portion based on an operation by the mouth of the user and disposed proximate to the second end of the extending portion, the control mechanism comprising:
a range finder configured to measure a distance between the stylus and the touch screen device; and
a processor configured to control the motor and rotate the power screw relative to the nut based on the distance measured by the range finder.

5. An extendable stylus configured to be operated with a mouth, the extendable stylus comprising:
an extending portion configured to have an adjustable length, the extending portion comprising:
a linear portion having the conductive tip connected to a first end thereof;
a nut disposed at a second end of the linear portion opposite the first end;
a power screw, which screwingly engages the nut disposed at the second end of the linear portion, wherein the power screw is rotatable relative to the nut and linear portion; and
a motor configured to rotate the power screw relative to the nut and the linear portion;
a conductive tip configured to interface with a touch screen device, wherein the conductive tip is disposed at a first end of the extending portion;
a mouthpiece configured to engage the mouth of a user, wherein the mouthpiece is disposed at a second end of the extending portion, opposite the first end; and
a control mechanism configured to control the length of the extending portion based on an operation by the mouth of the user and disposed proximate to the second end of the extending portion, the control mechanism comprising:
an IR sensor incorporated into the mouthpiece and configured to measure infrared radiation; and
a processor configured to control the motor to rotate the power screw relative to the nut when a change in IR radiation sensed by the IR sensor exceeds a threshold.

6. An extendable stylus configured to be operated with a mouth, the extendable stylus comprising:
an extending portion configured to have an adjustable length, the extending portion comprising:
a linear portion having the conductive tip connected to a first end thereof;
a nut disposed at a second end of the linear portion opposite the first end;
a power screw, which screwingly engages the nut disposed at the second end of the linear portion, wherein the power screw is rotatable relative to the nut and linear portion; and a motor configured to rotate the power screw relative to the nut and the linear portion;

a conductive tip configured to interface with a touch screen device, wherein the conductive tip is disposed at a first end of the extending portion;

a mouthpiece configured to engage the mouth of a user, wherein the mouthpiece is disposed at a second end of the extending portion, opposite the first end; and a control mechanism configured to control the length of the extending portion based on an operation by the mouth of the user and disposed proximate to the second end of the extending portion, the control mechanism comprising:

a wireless receiver incorporated into the stylus and configured to receive a wireless signal from a wireless control device; and a processor configured to control the motor to rotate the power screw relative to the nut based on the wireless signal received by the wireless receiver.

7. An extendable stylus configured to be operated with a mouth, the extendable stylus comprising:

an extending portion configured to have an adjustable length, the extending portion comprising:

a stationary portion;

a movable portion movable relative to the stationary portion;

a locking mechanism configured to hold the movable portion in a fixed position relative to the stationary portion, wherein the mouthpiece comprises a fixed mouthpiece portion and an articulating mouthpiece portion hingedly connected to the fixed mouthpiece portion, wherein the control mechanism comprises a lever arm attached to the articulating mouthpiece portion, wherein the lever arm is mechanically coupled to the locking mechanism and biased radially away from the lever arm by biasing force provided by a biasing member, and wherein the locking mechanism is released when the articulating mouthpiece portion is pressed toward the fixed mouthpiece portion with sufficient force to overcome the bias force provided by the biasing member, and a conductive tip configured to interface with a touch screen device, wherein the conductive tip is disposed at a first end of the extending portion;

a mouthpiece configured to engage the mouth of a user, wherein the mouthpiece is disposed at a second end of the extending portion, opposite the first end; and a control mechanism configured to control the length of the extending portion based on an operation by the mouth of the user and disposed proximate to the second end of the extending portion.

8. An extendable stylus configured to be operated with a mouth, the extendable stylus comprising:

an extending portion configured to have an adjustable length, the extending portion comprising:

a first linear piece, having a first end and a second end, wherein the conductive tip is connected to a first end thereof;

a second linear piece, having a first end and a second end, wherein the mouthpiece is connected to the first end thereof, and wherein the second end of one of the first linear piece and the second linear piece overlaps, and is configured to move linearly relative to, the other of the first linear piece and the second linear piece;

a biasing member configured to apply a biasing force to the first linear piece to move the first linear piece away from the mouthpiece;

a tensioning member configured to apply a tensioning force to the first linear piece to move the first linear piece toward the mouthpiece;

a spool, wherein the tensioning member is wrapped around the spool such that rotation of the spool in a first angular direction reduces a length of the tensioning member and rotation of the spool in a second angular direction increases the length of the tensioning member;

a motor configured to rotate the spool in at least one of the first angular direction and the second angular direction, and a conductive tip configured to interface with a touch screen device, wherein the conductive tip is disposed at a first end of the extending portion;

a mouthpiece configured to engage the mouth of a user, wherein the mouthpiece is disposed at a second end of the extending portion, opposite the first end; and a control mechanism configured to control the length of the extending portion based on an operation by the mouth of the user and disposed proximate to the second end of the extending portion.

9. The extendable stylus according to claim 8, wherein the control mechanism comprises a first bite sensor disposed in a first portion of the mouthpiece and a second bite sensor disposed in a second portion of the mouthpiece;

wherein the first bite sensor is configured to cause the motor to rotate in the first angular direction in response to sensing a pressure in the first portion of the mouthpiece; and wherein the second bite sensor is configured to cause the motor to rotate in the second angular direction in response to sensing a pressure in the second portion of the mouthpiece.

10. The extendable stylus according to claim 8, wherein the control mechanism comprises a tongue paddle connected to a first portion of the mouthpiece;

wherein the tongue paddle is configured to cause the motor to rotate in the first angular direction when the tongue paddle is manipulated in a first linear direction; and wherein the tongue paddle is configured to cause the motor to rotate in second angular direction when the tongue paddle is manipulated in a second linear direction different from the first direction.

11. The extendable stylus according to claim 8, wherein the control mechanism comprises:

a range finder configured to measure a distance between the stylus and the touch screen device; and a processor configured to control the motor and rotate the spool based on the distance measured by the range finder.

12. The extendable stylus according to claim 8, wherein the control mechanism comprises:

an IR sensor incorporated into the mouthpiece and configured to measure infrared radiation; and a processor configured to control the motor to rotate the spool when a change in IP radiation sensed by the IR sensor.

13. The extendable stylus according to claim 8, wherein the control mechanism comprises:

a wireless receiver incorporated into the stylus and configured to receive a wireless signal from a wireless control device; and a processor configured to control the motor to rotate the spool based on the wireless signal received by the wireless receiver.

14. The extendable stylus according to claim 8, wherein the control mechanism comprises:

an airflow sensor configured to determine a direction of air flowing proximate to the mouthpiece; and a processor configured to control the motor to rotate the spool based on the determined direction of air flowing proximate to the mouthpiece.

15. An extendable stylus configured to be operated with a mouth, the extendable stylus comprising:

an extending portion configured to have an adjustable length;

a conductive tip configured to interface with a touch screen device, wherein the conductive tip is disposed at a first end of the extending portion and is electrically connected to the mouthpiece;

a mouthpiece configured to engage the mouth of a user, wherein the mouthpiece is disposed at a second end of the extending portion, opposite the first end; and a control mechanism configured to control the length of the extending portion based on an operation by the mouth of the user and disposed proximate to the second end of the extending portion.

16. A system for allowing operation of a touch screen device using a mouth, the system comprising:

an extendable stylus configured to be operated with the mouth, the extendable stylus comprising:

an extending portion configured to have an adjustable length;

a conductive tip configured to interface with the touch screen device, wherein the conductive tip is disposed at a first end of the extending portion;

a mouthpiece configured to engage the mouth of a user, wherein the mouthpiece is disposed at a second end of the extending portion, opposite the first end; and a control mechanism disposed at or proximate to the second end of the extending portion, wherein the control mechanism is configured to control the length;

a first sensor configured to sense a first mouth operation and be removably attached to the extendable stylus;

a second sensor configured to sense a second mouth operation and be removably attached to the extendable stylus, wherein one of the first sensor and the second sensor is selected to be attached to the extendable stylus based on a physical capability of the user; and wherein the control mechanism is configured to control the length of the extending portion based on one of the first mouth operation and the second operation of the selected one of the first sensor and the second sensor.

17. The system of claim 16, wherein the extending portion of the extendable stylus comprises:

a linear portion having the conductive tip connected to a first end thereof;

a nut disposed at a second end of the linear portion opposite the first end;

a power screw, which screwingly engages the nut disposed at the second end of the linear portion; wherein the power screw it rotatable relative to the nut and linear portion;

a motor configured to rotate the power screw relative to the nut and the linear portion;

wherein the mouthpiece is connected to power screw by the motor; and wherein the control mechanism comprises a processor configured to control the motor to rotate the power screw relative to the nut.

18. The system of claim 16, wherein the extending portion of the extendable stylus comprises:

a first linear piece, having a first end and a second end, wherein the conductive tip is connected to a first end thereof;

a second linear piece, having a first end and a second end, wherein the mouthpiece is connected to the first end thereof, and wherein the second end of one of the first linear piece and the second linear piece overlaps, and is configured to move linearly relative to, the other of the first linear piece and the second linear piece;

a biasing member configured to apply a biasing force to the first linear piece to move the first linear piece away from the mouthpiece;

a tensioning member configured to apply a tensioning force to the first linear piece to move the first linear piece toward the mouthpiece;

a spool, wherein the tensioning member is wrapped around the spool such that rotation of the spool in a first angular direction reduces a length of the tensioning member and rotation of the spool in a second angular direction increases the length of the tensioning member;

a motor configured to rotate the spool in at least one of the first angular direction and the second angular direction; and wherein the control mechanism comprises a processor configured to control the motor to rotate the power screw relative to the nut.

19. The system of claim 16, wherein the conductive tip is electrically connected to the mouthpiece.

* * * * *